(12) United States Patent
Castro et al.

(10) Patent No.: US 6,469,173 B1
(45) Date of Patent: Oct. 22, 2002

(54) ALKYL ESTERS OF 3-(3,4-DIHALOGENOPHENYL)-2,6-DIOXOPIPERIDINE-3-PROPIONIC ACID OF USE AS INTERMEDIATES

(75) Inventors: Bertrand Castro, Saint Aunes; Jean-Robert Dormoy, Sisteron; Alain Rabion, Montpellier, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/857,882

(22) PCT Filed: Dec. 1, 1999

(86) PCT No.: PCT/FR00/02970

§ 371 (c)(1),
(2), (4) Date: Jun. 12, 2001

(87) PCT Pub. No.: WO00/37445

PCT Pub. Date: Jun. 29, 2000

(30) Foreign Application Priority Data

Dec. 18, 1998 (FR) .............................. 98 16087

(51) Int. Cl.$^7$ ............................. C07D 211/40
(52) U.S. Cl. ........................................ 546/220
(58) Field of Search ......................... 546/220

(56) References Cited

U.S. PATENT DOCUMENTS

| 5,741,910 A | 4/1998 | Bichon et al. | 546/193 |
| 5,942,523 A | 8/1999 | Bichon et al. | 514/329 |
| 6,008,360 A | 12/1999 | Camus et al. | 546/257 |

FOREIGN PATENT DOCUMENTS

| EP | 673928 | | 9/1995 |
| WO | WO 97/32852 | | 9/1997 |
| WO | 9732852 | * | 9/1997 |
| WO | WO 98/05640 | | 2/1998 |
| WO | WO 99/01451 | | 1/1999 |

* cited by examiner

Primary Examiner—Alan L. Rotman
Assistant Examiner—Binta Robinson
(74) Attorney, Agent, or Firm—Michael D. Alexander; Paul E. Dupont

(57) ABSTRACT

The invention relates to lower-alkyl esters of 3-(3,4-dihalophenyl)-2,6-dioxopiperidine-3-propionic acid derivatives, and to processes for preparing the same.

12 Claims, No Drawings

ALKYL ESTERS OF 3-(3,4-DIHALOGENOPHENYL)-2,6-DIOXOPIPERIDINE-3-PROPIONIC ACID OF USE AS INTERMEDIATES

The subject matter of the present invention is a lower alkyl ester of 3-(3,4-dihalophenyl)-2,6-dioxopiperidine-3-propionic acid. The invention also relates to a process for the preparation of this compound and to the use of said compound in preparing the corresponding acid.

3-(3,4-Dichlorophenyl)-2,6-dioxopiperidine-3-propionic acid is disclosed in Patent Application WO 97/32852. According to this patent application, 3-(3,4-dichlorophenyl)-2,6-dioxopiperidine-3-propionic acid can be reduced, for example by borane, to give 3-(3,4-dichlorophenyl)-3-(3-hydroxypropyl)piperidine. The latter compound, disclosed in Patent Application EP-A-673 928, is an intermediate of use in the preparation of osanetant. Osanetant is a specific antagonist of $NK_3$ receptors described, in particular, by X. Emonds-Alt in Life Sci., 1995, 56 (1), 27–32.

The novel compound of formula:

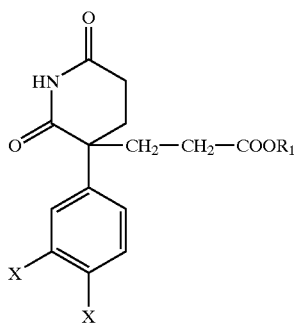

(I)

in which:
- X represents a halogen, preferably a chlorine or fluorine atom;
- $R_1$ represents a linear $C_1$–$C_4$ alkyl, preferably a methyl;

has now been found.

The present invention relates very particularly to the compound of formula (I) in which X=Cl and $R_1$=$CH_3$.

The invention comprises the compound of formula (I) in the racemic form and in the optically pure form.

The compound of S configuration corresponding to the formula:

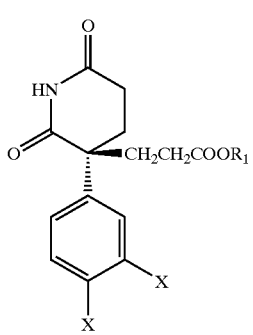

(II)

in which $R_1$ and X are as defined above for (I), is particularly preferred.

According to the present invention, in order to prepare the compound of formula (I), an acid of formula:

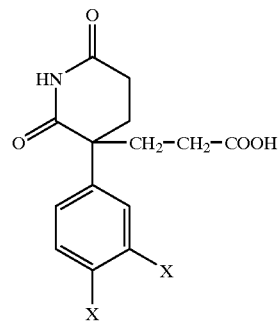

(III)

in which X is as defined for (I), is esterified. The compounds of formula (III) are disclosed in Patent Application WO 97/32852.

The esterification is carried out by conventional means well known to a person skilled in the art. For example, by the action of an alcohol in an acidic and anhydrous medium or alternatively by the action of thionyl chloride, to prepare the chloride of the acid of formula (III) as an intermediate, and then by the action of an alcohol of formula $R_1OH$, in which $R_1$ is as defined above for (I).

According to the process of the invention, the optical isomer of formula (II) can be prepared in the optically pure form by a process characterized in that an enantioselective enzymatic hydrolysis of the compound of formula:

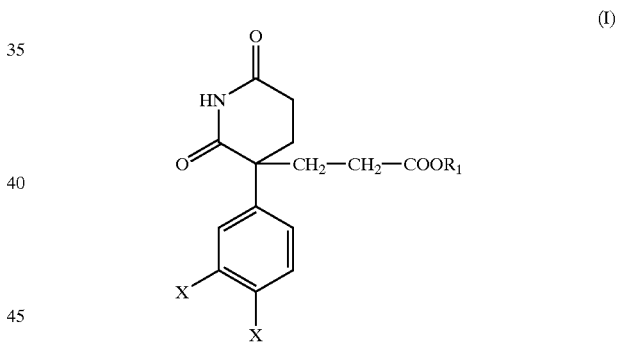

(I)

is carried out.

Thus, the racemic compound of formula (I) is hydrolyzed by an enzyme chosen from lipases, proteases or esterases, lipases or esterases being preferred.

Mention may be made, as nonlimiting examples, of lipases or esterases of *Candida cylindracea, Candida rugosa, Pseudomonas flurorescens, Humilica lanuginosa* or *Candida lipolytica*, α-chymotripsin or pig liver esterase.

Preference is given to the esterase or the lipase of *Candida rugosa*, or of *Candida cylindracea*, separately or as a mixture.

These enzymes are used in the purified form or in the form of crude extracts. The enzymes may or may not be attached to a support.

The hydrolysis reaction is carried out according to the following reaction scheme:

Scheme 1

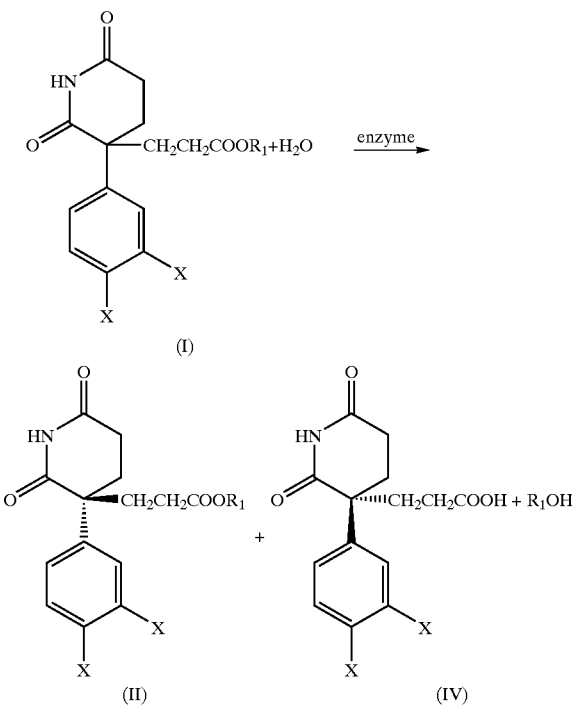

The enzymatic hydrolysis according to the invention is carried out in a medium comprising water and an organic solvent. The organic solvent can be nonpolar or moderately polar, such as a $C_1$–$C_{10}$ ether, a $C_1$–$C_{10}$ alkane, a $C_1$–$C_{10}$ tertiary alcohol, a $C_1$–$C_{10}$ ketone, a $C_1$–$C_{10}$ sulfoxide or furan, or, in some cases, a chlorinated solvent, such as dichloromethane, these solvents being used pure or as a mixture.

Preferably, use is made of a $C_1$–$C_{10}$ aliphatic ether, very particularly of methyl tert-butyl ether.

The water necessary for the hydrolysis can be dissolved in the reaction medium by a polar cosolvent or alternatively, preferably, the water constitutes a separate phase, the hydrolysis reaction then being carried out in a two-phase medium.

Thus, it is very particularly preferable to carry out the reaction in a two-phase medium composed of methyl tert-butyl ether (MTBE) and water. The MTBE/water ratio can vary from 1/99 to 99/1; a ratio of the order of 40/60 to 50/50, very particularly 44/56, is preferred.

The water used can be buffered or unbuffered and its pH can vary from 4 to 10 approximately; use is preferably made of water with a pH of the order of 5 to 8.

The concentration of diester in the reaction medium can vary in the proportions [lacuna] 1 to 500 g/l and preferably from 1 to 150 g/l, where the amount of enzyme varies in proportions from 0.0001 to 150 g/l and preferably from 1 to 50 g/l.

The temperature of the enzymatic hydrolysis reaction can vary between 0° C. and +50° C. and preferably between +16° C. and +35° C.

The duration of the reaction is between 3 hours and 36 hours, generally in the region of 10 hours.

The chiral ester of formula (II) is isolated by extraction, after having precipitated and then filtered off the enzyme used.

According to the present invention, a compound of formula (II) can also be prepared by a process consisting in carrying out a cyclization of the compound of formula:

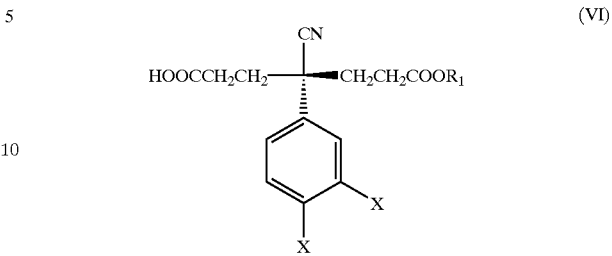

in which $R_1$ and X are as defined above for (I).

The cyclization of the compound of formula (VI) is carried out either thermally or in the presence of a catalyst.

Thus, a thermal cyclization can be carried out between 170° C. and 250° C., either in a molten medium or in the presence of a solvent, for example an inert solvent, such as toluene, DMSO, sulfolane or tetralin. The thermal cyclization is preferably carried out in a molten medium at a temperature in the region of 200° C.

The cyclization can also be carried out in the presence of a catalyst, such as an acid anhydride, for example acetic anhydride, phosphorus pentoxide, triflic anhydride, trifluoroacetic anhydride or methanesulfonic anhydride, or an acid, such as methanesulfonic acid or triflic acid, or a mixture of an acid anhydride and of an acid.

It is preferable to use, as catalyst, methanesulfonic anhydride and methanesulfonic acid or triflic anhydride and triflic acid.

The cyclization reaction is carried out at a temperature of between 20° C. and 130° C., preferably between 70° C. and 120° C.

Catalytic cyclization, which makes it possible to retain the optical purity, is preferably used in carrying out the cyclization of the compound of formula (VI).

The compound of formula (II) is isolated from the medium by extraction using conditions known to a person skilled in the art.

The compound of formula (VI) is obtained by a process consisting in treating, by an enzyme, a compound of formula

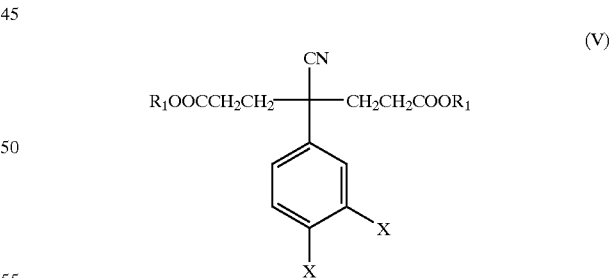

in which $R_1$ and $X_1$ are as defined above for (I).

The preparation of a compound of formula (V) is disclosed in Patent Applications EP-A-673 928 and WO 97/32852.

To convert the racemic diester of formula (V) to the chiral hemiester of formula (VI), an enantioselective enzymatic hydrolysis is carried out while choosing conditions similar to those described above.

The chiral hemiester of formula (VI) is isolated from the medium either by selective extraction or by precipitation after acidification of the aqueous phase.

The compound of the formula (VI) is novel and constitutes a further aspect of the present invention.

According to a further aspect, the present invention relates to the use of a compound of formula (II) in the preparation of a compound of formula:

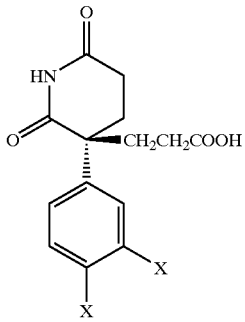

(VII)

in which X is as defined above;

the hydrolysis of an ester of formula (II) being carried out under conditions which make it possible to retain the stereochemistry of the 3-carbon of the piperidinedione. Thus, use may be made of the action of an acid, for example the action of a carboxylic acid in the presence of an inorganic acid, preferably acetic acid in the presence of hydrochloric acid.

Thus, the present invention relates to a process for the preparation of a compound of formula (VII) by hydrolysis of an ester of formula (II).

According to another aspect, the present invention relates to the use of a compound of formula (II) in the preparation of a compound of formula:

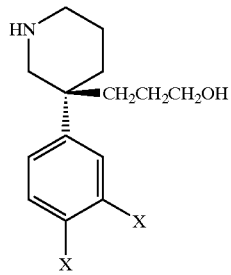

(VIII)

The reduction of the compound of formula (II) to a compound of formula (VIII) can be carried out by the action of a reducing agent.

The reducing agents used are borane complexes, such as, for example, borane-tetrahydrofuran or borane-dimethyl sulfide, or alternatively a mixed alkaline hydride, such as lithium aluminum hydride or sodium bis(2-methoxyethoxy) aluminum hydride in solution in toluene (Red-Al®). These reductions take place without racemization; the preferred reducing agent is the borane-tetrahydrofuran complex.

The reduction with borane is carried out in a solvent, preferably an aprotic solvent, such as tetrahydrofuran, at the reflux temperature of the solvent. The reduction is generally complete after heating for 1 to 6 hours and the 3,3-disubstituted piperidine is isolated according to conventional methods, the excess borane first being destroyed with methanol. The free base can be isolated by evaporation of the solvent and then the residue is taken up in water, acidification is carried out with hydrochloric acid, treatment is carried out with a base, preferably sodium hydroxide, and extraction is carried out with a solvent.

The free base of formula (VIII) can be converted to one of its salts according to well known techniques. The borane used for the reduction can be generated in situ according to conventional methods.

Thus, the present invention relates to a process for the preparation of a compound of formula (VIII) by reduction of a compound of formula (II).

Finally, according to another aspect, the present invention relates to the use of a compound of formula (VI) in the preparation of a compound of formula:

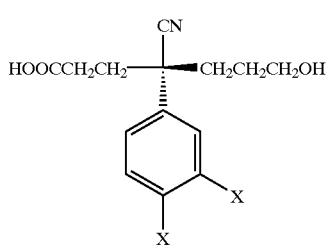

(IX)

in which X is as defined above for (I), by reduction in the presence of an alkaline hydride, such as, for example, LiAlH$_4$ or LiAlH$_3$ in methanol.

A compound of formula:

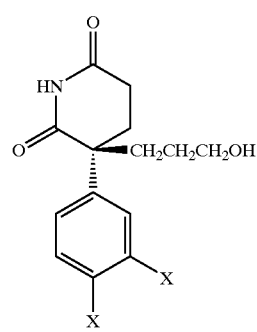

(X)

is prepared by cyclization of the compound of formula (IX) under the conditions described above.

The compound of formula (IX) is novel and forms part of the invention.

The compound of formula (X) is disclosed in International Patent Application WO 98/05640.

Thus, the present invention relates to a process for the preparation of a compound of formula (IX) by reduction of a compound of formula (VI).

In the present description, the following abbreviations are used:

DMSO: dimethyl sulfoxide
MTBE: methyl tert-butyl ether
TFH: tetrahydrofuran
iso ether: isopropyl ether
AT: ambient temperature
HPLC: high pressure liquid chromatography
IR: infrared
NMR: nuclear magnetic resonance at 250 or 300 MHz
δ: chemical shift, expressed in ppm
s: singlet; d: doublet; d of d: doublet of doublet;
m: multiplet or unresolved peak.

The following examples illustrate the invention.

EXAMPLE 1

Methyl Ester of 3-(3,4-Dichlorophenyl)-2,6-dioxopiperidine-3-propionic Acid 33 g of 3-(3,4-dichlorophenyl)-2,6-dioxopiperidine-3-propionic acid are placed in 300 ml of methanol and 1.5 g of $H_2SO_4$ in a 500 ml round-bottomed flask and then the mixture is heated at reflux for 45 minutes. The methanol is evaporated and then the residue is taken up in 300 ml of ether and stirred for 2 hours at AT. The precipitate formed is filtered off, rinsed with iso ether and then dried under vacuum at 40° C. 29.6 g of the expected ester are obtained. Yield 86%.

NMR (DMSO) (solvent δ $^1$H: 2.5 ppm) δ: 11 (s, 1H); 7.26–7.65 (m, 3H); 3.51 (s, 3H); 2.06–2.51 (m, 8H).

EXAMPLE 2

Methyl Ester of 3-(3,4-Dichlorophenyl)-2,6-dioxopiperidine-3-propionic Acid, (+) Isomer (Process 1)

5 g of *Candida cylindracea* L034 lipase (Biocatalysts), in suspension in 25 ml of 0.1M pH 7.0 phosphate buffer, are added to 1 g of methyl ester of racemic 3-(3,4-dichlorophenyl)-2,6-dioxopiperidine-3-propionic acid in 20 ml of MTBE (50 g/l). The reaction mixture is thermostatically controlled at 40° C. and stirred for 5 hours. The progress of the reaction is monitored by HPLC. After reacting for 5 hours, 48% of the starting material is hydrolyzed; the reaction is halted. 80 ml of MTBE are added to the reaction mixture and the latter is placed in ice, and 90 ml of acetone are incorporated in order to precipitate the enzyme. The precipitate is filtered off on a cellulose filter and then the organic solvents are evaporated. 2 equivalents of triethylamine are added to the remaining aqueous phase in order to bring the pH of the medium to 8.5. The non-hydrolyzed ester is extracted with 3×25 ml of dichloromethane. The dichloromethane phase is dried over anhydrous magnesium sulfate. After filtering and evaporating the dichloromethane to dryness (under vacuum), 500 mg of a yellow gum are isolated, corresponding to the expected compound (purity 96% by HPLC analysis). Extraction to an acidic pH is subsequently carried out. 25 ml of dichloromethane and 2 ml of 1N $H_2SO_4$ are added to the aqueous phase, with stirring and then extraction is carried out twice with 25 ml of dichloromethane. The organic phase is dried over anhydrous magnesium sulfate, filtered and evaporated to dryness under vacuum. 450 mg of white solid are obtained, analyzed by HPLC: 100% of 3-(3,4-dichlorophenyl)-2,6-dioxopiperidine-3-propionic acid, (−) isomer.

NMR (DMSO) (solvent δ $^1$H: 2.5 ppm): 3-(3,4-Dichlorophenyl)-2,6-dioxopiperidine-3-propionic acid, (−) isomer: δ: 12.10 (s, 1H); 11.0 (s, 1H); 7.66 (d, 1H); 7.55 (d, 1H); 7.28 (dd, 1H), 2.50–2.40 (m, 2H); 2.25–2.0 (m, 6H). Expected compound:

δ: 11.0 (s, 1H); 7.66 (d, 1H); 7.55 (d, 1H); 7.28 (dd, 1H), 3.52 (s, 3H); 2.50–2.40 (m, 2H); 2.35–2.0 (m, 6H) 3-(3,4-Dichlorophenyl)-2,6-dioxopiperidine-3-propionic acid, (−) isomer. $\alpha_D^{20}$=−105 (c=0.25, methanol).

Expected compound: $\alpha_D^{20}$=+119 (c=0.25, methanol).

EXAMPLE 3

Methyl Ester of 3-(3,4-Dichlorophenyl)-2,6-dioxopiperidine-3-propionic Acid, (+) Isomer (Process 2)

A)

Monomethyl Ester of 4-Cyano-4-(3,4-dichlorophenyl)-heptanedioic Acid, (−) Isomer To 12 g of dimethyl ester of 4-cyano-4-(3,4-dichlorophenyl)heptanedioic acid are dissolved in 53 ml of MTBE and 1 g of *Candida cylindracea* L034 lipase (Biocatalyst) are dissolved in 66 ml of 50 mM pH 7 phosphate buffer. The two solutions are mixed in a 500 ml three-necked round-bottomed flask. The reaction mixture is stirred vigorously, so as to create an emulsion. The temperature is set at 20° C. The reaction is halted after 5 hours. The progress of the reaction is monitored by HPLC.

The monomethyl ester is separated as follows: 240 ml of acetone are added to the reaction mixture and the medium is placed at 5° C. for 2 hours in order to precipitate the lipase. After 2 hours, the precipitate is filtered on a cellulose filter. The organic solvents are evaporated from the liquid phase under reduced pressure. The resulting aqueous phase is basified to pH 9 (NaHCO$_3$) and extracted with toluene (240 ml). The toluene phase is evaporated to dryness. This results in a powder comprising 90% of starting dimethyl ester and 10% of expected monomethyl ester. The aqueous phase is acidified to pH 2.5 (1N HCl) and then extracted with $CH_2Cl_2$ (240 ml). After evaporating, the expected monomethyl ester is isolated in the form of a white powder: 7.8 g. Purity: 99%.

The monomethyl ester can also be separated in the following way:

At the end of the reaction, the mixture is basified at pH=9 by addition of sodium hydroxide and then the aqueous phase and the organic phase are separated by settling. The organic phase is acidified up to pH=2.5 by addition of HCl. A precipitate which corresponds to the hemiester is formed and is recovered by filtration.

The hemiester can be purified by recrystallization from acetonitrile.

| Percentage analysis: | C | H | N |
|---|---|---|---|
| Theory | 52.34 | 4.32 | 4.06 |
| Measured | 52.24 | 4.33 | 4.10 |

Melting point: 110.2° C. IR (nujol) : 2238 cm$^{-1}$ (nitrile); 1740 cm$^{-1}$ (ester), 1693 cm$^{-1}$ (carboxylic acid); NMR (DMSO): δ; 12.30 (s, 1H); 7.73 (d, 1H); 7.72 (d, 1H); 7.46 (dd, 1H); 3.51 (s, 3H); 2.40–2.28 (m, 4H); 2.35 (m, 1H); 2.25 (m, 1H); 2.07 (m, 1H); 1.95 (m, 1H); $^{13}$C NMR (DMSO): δ: 173.3, 172.2, 138.3, 132.5, 131.7, 131.6, 128.6, 127.2, 121.1, 52.0, 47.0, 34.8, 34.7, 30.5, 30.3; $\alpha_D^{20}$=1.2 (c=1, MeOH).

B)

Methyl Ester of 3-(3,4-Dichlorophenyl)-2,6-dioxopiperidine-3-propionic Acid, (+Isomer)

1 g of the compound of stage A is introduced into a sealable Pyrex tube. The tube is placed under vacuum (water pump) and then sealed and brought to a temperature of 250° C. After reacting for 5 hours, the tube is cooled to ambient temperature and opened. The reaction product is dissolved in 6 ml of THF. After evaporating to dryness (under vacuum), the residue is dissolved in 50 ml of dichloromethane and the organic phase is washed with 3×50 ml of a 1M aqueous NaHCO$_3$ solution. After drying over anhydrous MgSO$_4$ and evaporating the dichloromethane under vacuum, 700 mg of expected compound are isolated in the form of a yellow oil (purity 94%, HPLC). The product is recrystallized from isopropyl ether (yield: 70%).;

Melting point: 105.5° C. $\alpha_D^{20}$=+62 (c=1, methanol/THF; 188/12; v/v).

Methyl Ester of 3-(3,4-Dichlorophenyl)-2,6-dioxopiperidine-3-propionic Acid, (+Isomer)

This compound can also be prepared by heating in the presence of methanesulfonic acid anhydride according to the process described below.

1 g of methanesulfonic acid anhydride and 60 mg of methanesulfonic acid (100%) are introduced into a 100 ml three-necked flask under a nitrogen stream. The mixture is heated until it melts. 1 g of the compound of stage A is added to the reaction medium and the combined mixture is brought to 100° C. The reaction is monitored by thin layer chromatography (CH$_2$Cl$_2$: MeOH, 95.5). After one hour, the reaction is halted. The medium is cooled to ambient temperature and the anhydride is hydrolyzed by the addition of water. The reaction product is extracted with dichloromethane and purified by washing with a 1M aqueous NaHCO$_3$ solution. After drying over anhydrous MgSO$_4$ and evaporating the dichloromethane under vacuum, the glutaramide ester is isolated in the form of a yellow oil. The expected product crystallizes slowly while exposed to the air: 0.85 g is obtained (HPLC analysis: chemical purity 98%). Melting point 105° C.

$\alpha_D^{20}$=+118° C. (c=0.25, methanol).

The thermal cyclization reaction takes place partially with racemization in comparison with the catalyzed cyclization reaction.

EXAMPLE 4

3-(3,4-Dichlorophenyl)-3-(3-hydroxypropyl)-piperidine Fumarate 17.2 g of methyl ester of 3-(3,4-dichlorophenyl)-2,6-dioxopiperidine-3-propionic acid are dissolved in 50 ml of THF under nitrogen. 200 ml of 1M borane in THF are added over 10 minutes at 10° C. After heating at reflux for 2 hours, an additional 60 ml of 1M borane in THF are added and heating is maintained at reflux for a further 1 hour. The excess borane is destroyed with methanol. After significant evolution of gas, the mixture is heated at reflux for 30 minutes and then the solvents are evaporated. The residue is taken up in 300 ml of water and 10 g of H$_2$SO$_4$ and then the mixture is heated at reflux for 2 hours and left overnight at AT. 25 ml of concentrated sodium hydroxide solution are added and then extraction is carried out (twice) with 80 ml of butanol. The organic phase is washed with 1000 ml of water and then concentrated, and the residue is taken up in 100 ml of isopropanol. Heating is carried out at reflux, salification is carried out by addition of 7 g of fumaric acid in 75 ml of isopropanol and the mixture is allowed to return to AT. The precipitate formed is filtered off and then dried under vacuum. 13.23 g of the expected compound are obtained.

The filtrates are concentrated and an additional 0.70 g of the expected compound is isolated. Overall yield: 81.5%.

EXAMPLE 5

3-(3,4-Dichlorophenyl)-2,6-dioxopiperidine-3-propionic Acid

Methyl Ester of 3-(3,4-dichlorophenyl)-2,6-dioxopiperidine-3-propionic [Lacuna], (+) Isomer This compound is prepared in Example 3, stage C.

B) 3-(3,4-Dichlorophenyl)-2,6-dioxopiperidine-3-propionic Acid 0.668 g of the compound of the preceding stage, 2 ml of acetic acid and 0.10 ml of concentrated hydrochloric acid are introduced into a 100 ml three-necked flask. The combined mixture is heated to 70° C. After 2 hours, the reaction product precipitates and the reaction is halted. After returning to ambient temperature, 2 ml of water are added to the reaction medium. The reaction product is filtered off on a sintered glass filter, washed with water and then recrystallized from acetic acid. 0.47 g of the expected compound is obtained. (Yield 70%).

$\alpha_D^{20}$=+117 (c=0.25, methanol).

EXAMPLE 6

4-Cyano-4-(3,4-dichlorophenyl)-7-hydroxyheptanoic Acid 231 mg of LiBH$_4$ and 30 ml of MTBE are introduced under a nitrogen stream and then 429 µl of methanol, diluted in 30 ml of MTBE, are added dropwise. 1 g of compound prepared in Example 3, stage A, in solution in 80 ml of MTBE ether, is added to the reaction medium and the combined mixture is heated at reflux. After three hours, the reaction medium is placed in ice and a 1N HCl solution is added. When there is no longer evolution of gas, the reaction product is extracted with dichloromethane. After drying over anhydrous magnesium sulfate and evaporating the solvent under vacuum, the product is isolated in the form of a white gum.

The product is recrystallized from 6 ml of toluene and 600 mg of an expected compound are obtained in the form of a white powder.

$\alpha_D^{20}$=−10.7 (c=1, methanol). NMR (DMSO) (solvent δ $^1$H: 2.5 ppm): δ: 12.30 (bs, 1H) ; 7.69 (d, 1H) ; 7.65 (d, 1H) ; 7.42 (dd, 1H); 4.5 (bs, 1H); 3.33 (t, 2H); 2.35–2.2 (m, 3H); 2.1–1.8 (m, 3H); 1.50–1.10 (m, 2H).

What is claimed is:

1. A compound of formula:

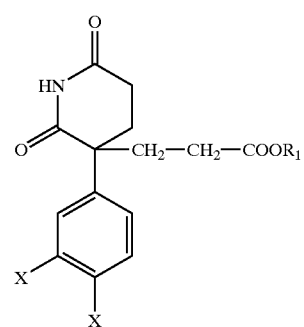

in which:

X represents a halogen,

R$_1$ represents a linear C$_1$–C$_4$ alkyl.

2. A compound according to claim 1 of formula (I), in which X represents a chlorine atom or a fluorine atom.

3. A compound according to claim 1 of formula (I), in which X=Cl and R$_1$=CH$_3$.

4. A compound according to claim 1 of S configuration corresponding to the formula:

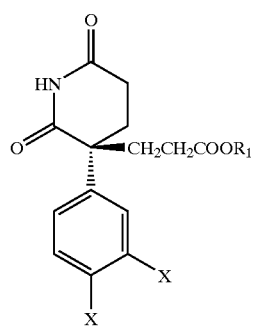

in which $R_1$ and X are as defined for (I) in claim 1.

5. A process for the preparation of a compound according to claim 1 wherein an acid of formula:

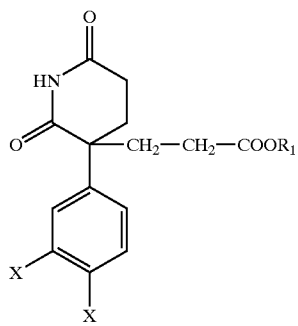

in which X is as defined for (I) in claim 1, is esterified.

6. A process for the preparation of a compound according to claim 4 which comprises carrying out a cyclization of the compound of formula:

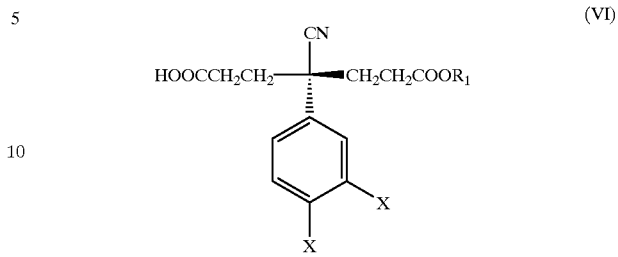

in which $R_1$ and X are as defined for (I) in claim 1.

7. A process according to claim 6 wherein the cyclization is carried out either in a molten medium between 170° C. and 250° C. or in the presence of a catalyst between 20° C. and 130° C.

8. A process according to claim 7 wherein the cyclization is carried out in a molten medium at a temperature in the region o 200° C.

9. A process according to claim 7 wherein the cyclization is carried out in the presence of an acid anhydride or of an acid, or of a mixture of an acid anhydride and of an acid.

10. A process according to claim 9 wherein the cyclization is carried out in the presence of methanesulfonic anhydride and of methanesulfonic acid or in the presence of triflic anhydride and of triflic acid.

11. A compound according to claim 4 wherein X represents a chlorine atom or a fluorine atom.

12. A compound according to claim 11 wherein X=Cl and $R_1$=$CH_3$.

* * * * *